US005458559A

United States Patent [19]

Gauntlett

[11] Patent Number: 5,458,559

[45] Date of Patent: Oct. 17, 1995

[54] ARTIFICIAL VAGINA

[76] Inventor: Arthur E. Gauntlett, "Whitehall", No. 1 Park Road PO Box HM 529, Hamilton HM CX, Bermuda

[21] Appl. No.: 244,822

[22] PCT Filed: Oct. 13, 1993

[86] PCT No.: PCT/GB93/02110

§ 371 Date: Jun. 13, 1994

§ 102(e) Date: Jun. 13, 1994

[87] PCT Pub. No.: WO94/08547

PCT Pub. Date: Apr. 28, 1994

[30] Foreign Application Priority Data

Oct. 13, 1992 [GB] United Kingdom ................... 9221504

[51] Int. Cl.[6] ........................................ A61F 5/00

[52] U.S. Cl. ........................................ 600/38; 128/830

[58] Field of Search ................................ 128/830–841, 128/842, 844, 918; 604/330, 347–353; 600/38

[56] References Cited

U.S. PATENT DOCUMENTS

| | | | |
|---|---|---|---|
| 3,589,364 | 6/1971 | Dean | 604/375 |
| 4,241,912 | 12/1980 | Mercer | 600/41 |
| 4,690,678 | 9/1987 | Douglas-Hamilton | 604/349 |
| 4,744,352 | 5/1988 | Emery | 604/349 |

*Primary Examiner*—Michael A. Brown
*Attorney, Agent, or Firm*—Shoemaker and Mattare, Ltd.

[57] ABSTRACT

An artificial vagina is described includes a sheath (1) made from a flexible waterproof material. The sheath tapers from one end to the other, the wider end having a resealable opening (2) closed by a screw-threaded stopper (3). Projecting from the inner end of stopper (3) is an eye loop (4) connected to a hook (5) which swivels on wire loop (6) secured to tab (7). The tapered end of sheath (1) has a soft flexible undulating wall (8) and a bulbous portion (9) from which extends an annular membrane (10), the peripheral edge of which has a reinforced elastic rib (11). When assembled with the hook (5) connected to wire loop (6) a fluid chamber (12) is formed and filled with warm water (13) forming a chamber (14). Aperture (15) is formed in wall (8) to connect with bulbous portion (9) for the passage of the water (13).

9 Claims, 1 Drawing Sheet

ARTIFICIAL VAGINA

BACKGROUND OF THE INVENTION

This invention relates to an artificial vagina and more particularly to a male sexual gratification device.

Due to the current worlwide risks of life threatening infections such as AIDS (Acquired Immunity Deficiency Syndrome) care must be exercised in sexual relationships by using protection such as condoms to prevent the spread of the infection. The alternatives to this are total abstinence from sexual intercourse, or self-gratification for prudent sexually unfulfilled mature males unable to attain otherwise satisfying monogamous relationships with consenting female partners.

Although devices of this type are available, they have the disadvantage that they are not 100% reliable from the point of view of hygiene.

SUMMARY OF THE INVENTION

An aim of the present invention is to overcome the above disadvantage and to provide a device which fulfills its purpose and is hygienically maintained.

According to the present invention there is provided an artificial vagina comprising a tapered sheath of flexible waterproof material, the larger end of which has an opening re-sealable by a removable closure member, the closure member having releasable means to connect with the other end of the sheath to pull this into the sheath so that a fluid chamber is formed between the inwardly folded end and the wall of the other end of the sheath.

Preferably, the closure member is a screw-threaded stopper, and the releasable means is a loop and swivel hook connection.

Conveniently, the outer wall of the sheath has an annular membrane, the inner circumference of which has a ring shaped reinforced elastic rib.

In a preferred construction the sheath is formed with a bulbous portion adjacent the annular membrane where it joins the sheath wall.

BRIEF DESCRIPTION OF THE INVENTION

An embodiment of the artificial vagina will now be described by way of example only, with reference to the accompanying drawings, in which.

DESCRIPTION OF THE PREFERRED EMBODIMENT

Figure 1:
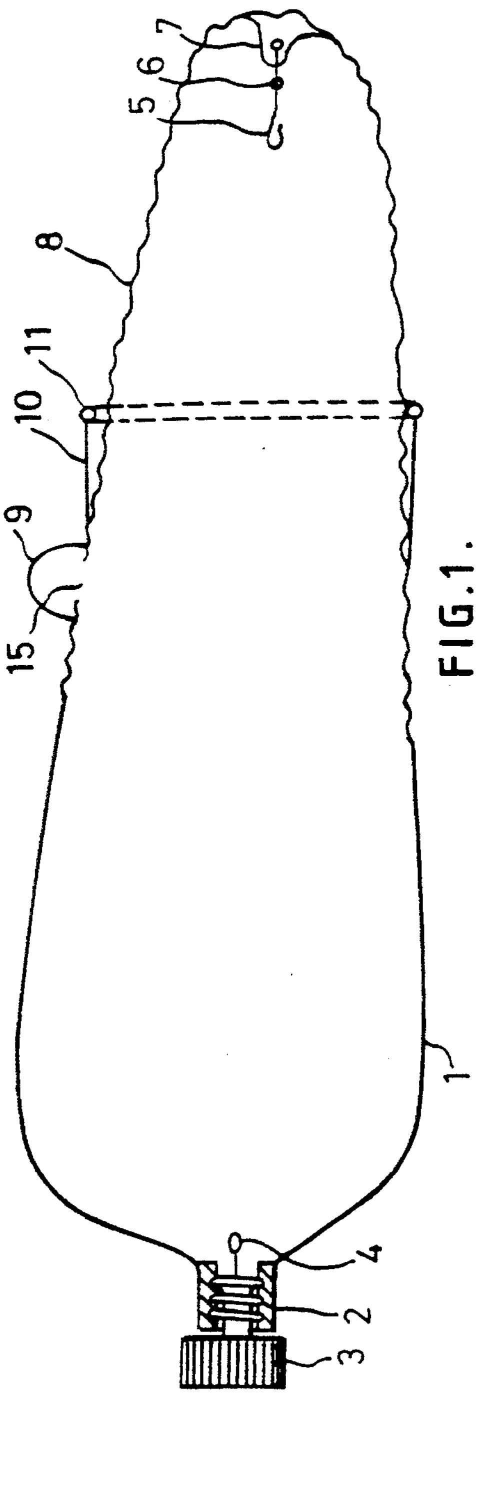
FIG. 1 is a diagrammatic longitudinal section of the artificial vagina according to the invention.
Figure 2:
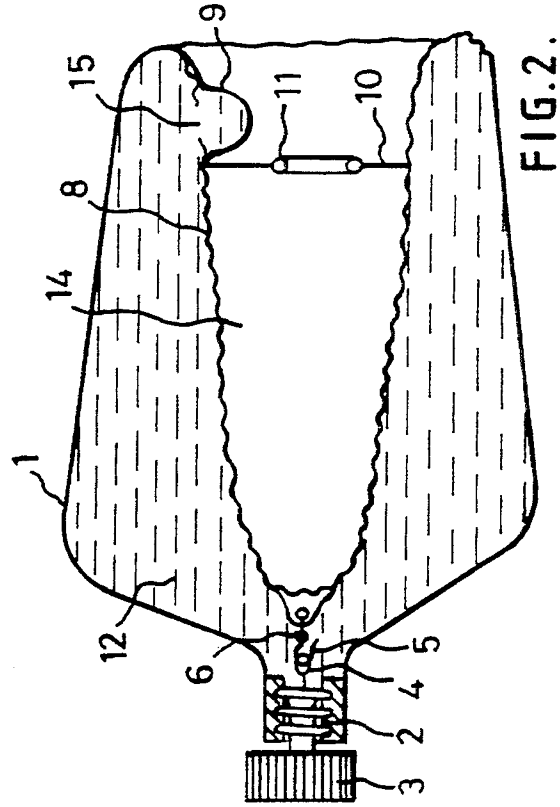
FIG. 2 is a longitudinal section of the artificial vagina in its assembled position for use.

The artificial vagina illustrated comprises a sheath 1 made from a flexible waterproof material such as rubber or an elastomeric plastics material. The sheath tapers from one end to the other, the wider end having a re-sealable opening 2 closed by a screw-threaded stopper 3 which screws into and forms a seal with a screw-thread moulded in the sheath opening 2. Projecting from the inner end of the stopper is an eye loop 4 which is connected to a hook 5 which swivels on a wire connection 6 secured to a tab 7 formed integral with the sheath 1.

The tapered end of the sheath 1 is moulded with a soft flexible portion formed with an undulating wall 8. Intermediate the ends of the sheath the wall has a bulbous portion 9 from which extends an annular membrane 10 the outer peripheral edge of which has a reinforced elastic rib 11 extending around the outside of the sheath 1.

To assemble the device the tapered end of the sheath is pushed into the wider end and the hook 5 is connected to the loop 4 carried by the stopper 3 to form an annular fluid chamber 12. The wire connection 6 allows the hook 5 to swivel while hooked to the eye loop 4 when the stopper 3 is tightened to seal the sheath opening 2. The chamber 12 is filled with warm water 13 or another suitable fluid through the opening 2 which is sealed by screwing in the stopper 3.

Figure 3:
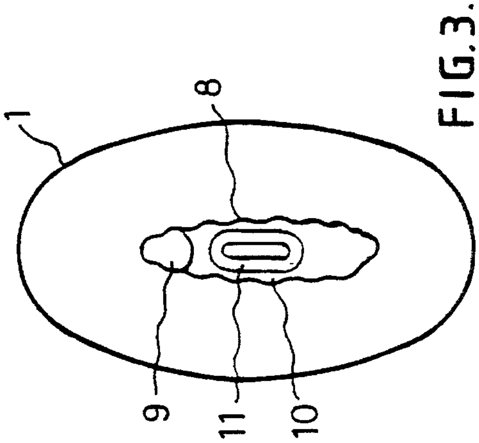
FIG. 3 is an end elevation of the artificial vagina shown in FIG. 2.

By inverting the tapered end of the sleeve a flexible chamber 14 is formed for receiving a male penis. To simulate the shape of a female vagina the bulbous portion 9 projects into the extrance of the chamber 12 to form a clitoris (see FIG. 3) and has an aperture 15 to allow the warm water from the chamber 12 to fill the bulbous portion 9.

The assembled sheath, when filled with warm water, becomes a warm soft envelope closely resembling a female vagina, clitoris, hymen and uterus and is thus capable of receiving a suitably lubricated male organ to stimulate the organ to an orgasm independent of the presence of a second party.

It will be obvious that various options are available for temporarily securing the artificial vagina to facilitate its effective use in whatever environment the device is chosen to be used. For example, it may be placed between the legs of a female partner who is unable to accommodate her partner during menstruation so that a vitally important physical and emotional loving relationship can be fully enjoyed.

The design of the device facilitates critically and necessary cleansing for reuse by simply unscrewing the stopper 3, releasing the hook 5 from the eye loop 4 and pouring the water from the sheath. The sheath is then inverted allowing careful cleansing of all the parts of the sheath.

The artificial vagina can be readily collapsed and laid flat for storage when not in use.

Various modifications may be made to the sheath. For example, it can be coloured, shaped or textured and may be decoratively embellished and of a size selected to most beneficially heighten the level of arousal of the male penis.

The artificial vagina has other medical uses. For example, it can be used to collect semen from the male in a course of artificial insemination.

What is claimed is:

1. An artificial vagina comprising a tapered sheath of a flexible waterproof material, the tapered sheath having a larger end, an outer wall and a smaller end, the larger end having a wall and an opening re-sealable by a removable closure member, the smaller end is adapted to be inwardly folded, the closure member having releasable means, connectable with the smaller end of the sheath, for pulling the smaller end into the larger end of the sheath so that a fluid chamber is formed between the inwardly-folded smaller end and the wall of the larger end of the sheath.

2. An artificial vagina as claimed in claim 1, where the closure member is a screw-threaded stopper, and the releasable means is a loop and swivel hook connection.

3. An artificial vagina as claimed in claim 2, wherein the outer wall of the sheath, where it is folded inwards, has an annular member whose inner circumference has a ring-shaped reinforced elastic rib.

4. An artificial vagina as claimed in claim 3, wherein a bulbous portion is formed in the sheath wall adjacent the annular membrane.

5. An artificial vagina as claimed in claim 4, wherein the bulbous portion has an aperture which connects a chamber formed by the bulbous portion with the fluid chamber when assembled for use.

6. An artificial vagina as claimed in claim 1, 2, 3, 4 or 5, wherein the smaller end of the sheath has undulating walls of a soft flexible material.

7. An artificial vagina as claimed in claim 1, wherein said flexible waterproof material is an elastomeric washable material.

8. An artificial vagina as claimed in claim 7, wherein said elastomeric washable material consists essentially of rubber.

9. An artificial vagina as claimed in claim 7, wherein said elastomeric washable material consists essentially of a flexible plastic material.

* * * * *

UNITED STATES PATENT AND TRADEMARK OFFICE

CERTIFICATE OF CORRECTION

PATENT NO. : 5,458,559

DATED : October 17, 1995

INVENTOR(S) : Gauntlett

It is certified that error appears in the above-indentified patent and that said Letters Patent is hereby corrected as shown below:

Title page: change "PCT/GB93/02110 to-- PCT/GB93/02118--.

Signed and Sealed this

Twelfth Day of December, 1995

Attest:

BRUCE LEHMAN

Attesting Officer

*Commissioner of Patents and Trademarks*